Feb. 22, 1966 J. R. LARUS ETAL Plant Pat. 2,604
GLADIOLUS PLANT
Filed Oct. 14, 1964
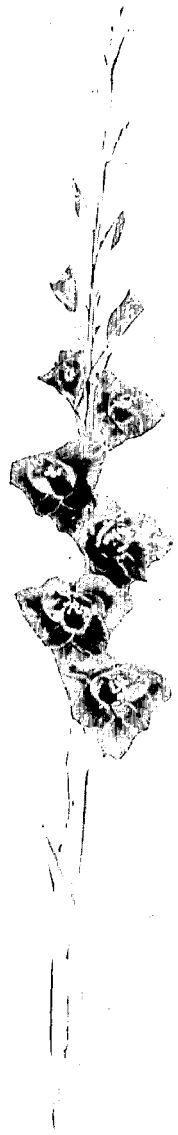
INVENTORS
John R. Larus
Charles T. Larus
By Lamont Johnston
ATTORNEY United States Patent Office Plant Pat. 2,604
Patented Feb. 22, 1966

2,604
GLADIOLUS PLANT

John R. Larus, West Hartford, and Charles T. Larus, Hartford, Conn., assignors to Selected Glads, Inc., New Albany, Ind., a corporation of Tennessee Filed Oct. 14, 1964, Ser. No. 403,964
1 Claim. (Cl. Plt.—85)

Our present invention relates to a new and improved variety of gladiolus and is notable for its bright red florets of small size on tall, tapering spikes.

To the best of our knowledge, this variety is the result of a cross between Parfait, the seed parent, and an unnamed seedling of Atom and Bo-Peep as the pollen parent (all unpatented).

This new variety has been asexually reproduced by us in Connecticut by natural increase from cormels through several generations and its characteristics have proven to be permanently fixed.

The illustration, made a part of this application, shows a single bloom spike, reduced in size, and is as nearly true to color as it is possible to depict. The illustration shows quite accurately the color, zigzag placement, bud formation and the small-size florets.

In the following detailed description, color plate references are to "The Horticultural Colour Chart" by the British Colour Council. Where there are other references to color, the ordinary dictionary meanings of the terms are intended.

*The plant*

Growth: Vigorous grower. Grows 40 to 50 inches high over-all.

Blooming: Blooms in about 70 days from large bulbs.

Stems: Slender, ¼ inch in diameter. Light rose color above corm.

Foliage: Medium green; upright. Leaves average 1 inch across. Plant foliage, excluding the flower spike, grows 26 to 28 inches in height.

Disease resistance: Above average resistance to disease.

Corms: Plump, irregular shaped, thin husk. Flesh and husk are light tan with a rose cast; flesh varies in rose shading from bulb to bulb. Husk is very glossy.

*The flower*

Spike: Flowerhead is 22 to 26 inches in length with eighteen to twenty-two buds of which six to eight open at one time.

Bud:

*Size.*—Opening buds are 1½ inches across.

*Opening.*—Four to six show color at one time.

Flower:

*Arrangement.*—Informal, zigzag placement on the spike.

*Size.*—Individual florets are 3 inches in diameter.

*Form.*—Triangular and slightly frilled.

*Keeping qualities.*—Opens well on the plant. Average opener from tight bud.

Petals:

*Shape.*—Triangular; frilled.

*Size.*—Upper petals are 1½ inches across; lip petals are ⅝-inch.

*Aspect.*—Light, leathery substance.

*Fragrance.*—None.

*Color.*—Blood Red 820/$_3$. Broad line in lip petals is Oxblood Red, 00823/$_2$.

Reproductive organs:

*Stamens.*—Light red; purple pollen.

*Pistil.*—Light red.

*Comparisons*

Our new variety resembles Torchy (unpatented), more than any other variety but differs from it principally as follows:

(1) It normally opens one more floret before the first one fades.

(2) It normally has one or two more unopened florets showing color.

(3) The florets are slightly smaller, being a little less wide open.

(4) It is more nearly a clear light red and does not have the rose red line in the middle of the throat petals.

(5) There is more tendency of the stems to show a slight waving.

(6) The flowerheads are longer.

Having thus disclosed our invention, we claim:

The new and distinct variety of gladiolus plant, substantially as herein shown and described, characterized by its clean, bright color of blossoms, its long flowerhead and its ability to open up to 8 florets at one time.

No references cited.

ABRAHAM G. STONE, *Primary Examiner.*

R. E. BAGWILL, *Assistant Examiner.*